United States Patent
Takami et al.

(10) Patent No.: US 7,490,968 B2
(45) Date of Patent: Feb. 17, 2009

(54) OPERATING STATE DISPLAY SYSTEM

(75) Inventors: Satoshi Takami, Saitama (JP); Hiroto Watanabe, Tokyo (JP)

(73) Assignee: Hoya Corporation, Tokyo (JP)

( * ) Notice: Subject to any disclaimer, the term of this patent is extended or adjusted under 35 U.S.C. 154(b) by 0 days.

(21) Appl. No.: 11/865,870

(22) Filed: Oct. 2, 2007

(65) Prior Publication Data
US 2008/0084683 A1    Apr. 10, 2008

(51) Int. Cl.
*F21V 8/00*    (2006.01)
(52) U.S. Cl. .................. 362/555; 362/558; 362/572
(58) Field of Classification Search .......... 362/574, 362/572, 559, 555, 558, 800
See application file for complete search history.

(56) References Cited

U.S. PATENT DOCUMENTS

| 4,188,654 | A  | * | 2/1980 | Reich et al. ............. 362/559 |
| 7,059,756 | B2 | * | 6/2006 | Prinz et al. ............. 362/559 |
| 7,111,953 | B2 | * | 9/2006 | Hunag et al. ............. 362/26 |
| 2003/0103359 | A1 | * | 6/2003 | Chiang et al. ............. 362/558 |
| 2004/0102680 | A1 | | 5/2004 | Sakaki |
| 2007/0039077 | A1 | | 2/2007 | Takami |
| 2007/0177385 | A1 | | 8/2007 | Sawada et al. |
| 2007/0206391 | A1 | * | 9/2007 | Matsuo et al. ............. 362/558 |

FOREIGN PATENT DOCUMENTS

JP    5-36483    5/1993
JP    11-153970    6/1999

OTHER PUBLICATIONS

English language Abstract of JP 5-364883.
English language Abstract of JP 11-153970.

* cited by examiner

*Primary Examiner*—Laura Tso
(74) *Attorney, Agent, or Firm*—Greenblum & Bernstein, P.L.C.

(57) ABSTRACT

An operating state display system includes a housing, a board provided inside the housing, a first light emitter attached on the board, a second light emitter arranged adjacent to the first light emitter on the board, a first light guider attached to the housing to face the first light emitter, a second light guider attached to the housing to face the second light emitter, and an electronic component attached between the first and second light emitters on the board. The electronic component protrudes by a predetermined length in the same direction as the first and second light emitters from a surface of the board. The predetermined length is longer than a distance between the first light emitter and the board and a distance between the second light emitter and the board.

11 Claims, 3 Drawing Sheets

OPERATING STATE DISPLAY SYSTEM

BACKGROUND OF THE INVENTION

The present invention relates to a system displaying an operating state of a device, particularly, to a system displaying a remaining battery level that is provided at a light source apparatus to be connected with an endoscope.

A light source apparatus to be connected with an endoscope is mainly provided with an illuminating device and a battery. The illuminating device emits light with power supply from the battery. The emitted light is transmitted through an optical fiber provided in the endoscope to illuminate a region to be observed. As a remaining amount of the battery is reduced due to use of the light source apparatus, the light source apparatus may not cause the illuminating device to emit the light unless a sufficient voltage is supplied thereto. In such a case, the light source device cannot be used as an illuminator for the endoscope. When the observed region comes into an unilluminated state while using the endoscope, it cannot be helped to break the observation. In order to prevent such undesirable observation break and maintain efficient observation, it is required to monitor the remaining battery level in use of the light source apparatus.

To solve the above problem, there is a light source apparatus provided with an operating state display system for displaying the remaining battery level. The operating state display system, which mainly includes a light emitter and light guider, lets a user know an operating state of the light source apparatus with light emitted by the light emitter. The light emitter is incorporated inside a housing, and the light guider is arranged to penetrate the housing and face the light emitter. The light emitted by the light emitter is incident onto a specific surface of the light guider, and emitted from a surface disposed out of an outer surface of the housing. In general, the operating state display system is configured with a plurality of pairs of the light emitter and light guider.

Meanwhile, when a pair of a light emitter and a light guider is located adjacent to another pair of ones such that the light emitters and light guiders are arranged side by side, respectively, light emitted by a light emitter of one light emitter/guider pair may be incident to the adjacent light guider of the other pair such that the adjacent light guider appears to light. When the user misunderstands the adjacent light guider lights, the user who cannot grasp a proper remaining battery level of the light source apparatus misjudges time left during which the illuminating device can emit the light. It results in inefficient endoscope observation. So as to avoid such misjudgment, there have been known a structure in which light emitted by a light emitter of one light emitter/guider pair is completely blocked by a light shielding wall not to be incident to the adjacent light guider of the other pair (Japanese Utility Model Provisional Publication No. HEI 5-36483) and a structure in which light emitted by a light emitter of one light emitter/guider pair is transmitted through a slit not to be incident to the adjacent light guider of the other pair (Japanese Patent Provisional Publication No. HEI 11-153970).

However, the aforementioned light shielding wall, configured to keep the light emitted by the light emitter of one light emitter/guider pair from being incident to the adjacent light guider of the other pair, transmits a force generated by a vibration to a substrate and cabinet as components of the operating state display system. Therefore, it causes an undesirable vibration sound and damage of the substrate. In addition, due to a hole such as the slit provided in the substrate, mechanical strength of the substrate is reduced and a product life is shorten. Further, adding a further component or process to the substrate incurs a rise in a manufacturing cost.

SUMMARY OF THE INVENTION

The present invention is advantageous in that there can be provided an improved operating state display system that prevents light emitted by a light emitter of a light emitter/guider pair from being incident to a light guider of an adjacent light emitter/guider pair and allows a user to monitor a proper operating state of a device (apparatus).

According to an aspect of the present invention, there is provided an operating state display system, which includes a housing, a board provided inside the housing, a first light emitter attached on the board, a second light emitter arranged adjacent to the first light emitter on the board, a first light guider attached to the housing to face the first light emitter such that light emitted by the first light emitter is transmitted therethrough to be emitted out of the housing, a second light guider attached to the housing to face the second light emitter such that light emitted by the second light emitter is transmitted therethrough to be emitted out of the housing, and an electronic component attached between the first and second light emitters on the board, the electronic component being configured to protrude from a surface of the board by a predetermined length in the same direction as the first and second light emitters, the predetermined length being longer than a distance between the first light emitter and the board and a distance between the second light emitter and the board.

Optionally, the first light guider may be arranged such that a portion thereof illuminated by the light emitted by the second light emitter is located out of a region where the light emitted by the second light emitter has a light intensity higher than half of a light intensity in a luminous point of the second light emitter.

Still optionally, the second light guider may be arranged such that a portion thereof illuminated by the light emitted by the first light emitter is located out of a region where the light emitted by the first light emitter has a light intensity higher than half of a light intensity in a luminous point of the first light emitter.

Optionally, the first light guider may include a first light receiving surface that faces the first light emitter to receive the light emitted by the first light emitter and a first light emitting surface exposed out of the housing to emit the light received by the first light receiving surface out of the housing. Optionally, the second light guider may include a second light receiving surface that faces the second light emitter to receive the light emitted by the second light emitter and a second light emitting surface exposed out of the housing to emit the light received by the second light receiving surface out of the housing.

Yet optionally, each of the first and second light guiders may be formed in a cylinder shape. In this case, the first light guider may include a first transmission surface as a side surface of the cylinder, and the second light guider may include a second transmission surface as a side surface of the cylinder.

Optionally, the electronic component may be configured to cover over the first and second light emitters in a direction that is perpendicular to an arranging direction of the first and second light guiders and parallel to the surface of the board.

Optionally, the electronic component may be formed in one of a rectangular parallelepiped shape and a cylinder shape.

Optionally, the electronic component may include a chip condenser.

According to another aspect of the present invention, there is provided an operating state display system, which includes a housing, a board provided inside the housing, a first light emitter attached on the board, a second light emitter arranged adjacent to the first light emitter on the board, a first light guider attached to the housing, the first light guider including a first light receiving surface that faces the first light emitter to receive light emitted by the first light emitter, a first light emitting surface exposed out of the housing to emit the light received by the first light receiving surface out of the housing, and a first transmission surface, and a second light guider attached to the housing, the second light guider including a second light receiving surface that faces the second light emitter to receive light emitted by the second light emitter, a second light emitting surface exposed out of the housing to emit the light received by the second light receiving surface out of the housing, and a second transmission surface. The first and second transmission surfaces are configured to block externally incident light.

Optionally, each of the first and second transmission surfaces may be configured with coating material being applied thereon to block the externally incident light.

Optionally, each of the first and second transmission surfaces may be configured with a cover being put thereon to block the externally incident light.

BRIEF DESCRIPTION OF THE ACCOMPANYING DRAWINGS

FIG. 1 schematically shows cross sections of an endoscope and light source apparatus in a first embodiment according to one or more aspects of the present invention.

FIG. 2 is a cross-sectional side view of an operating state display system in the first embodiment according to one or more aspects of the present invention.

FIG. 3 schematically shows a general directional characteristics of an LED.

DETAILED DESCRIPTION OF THE EMBODIMENTS

Figure 1:
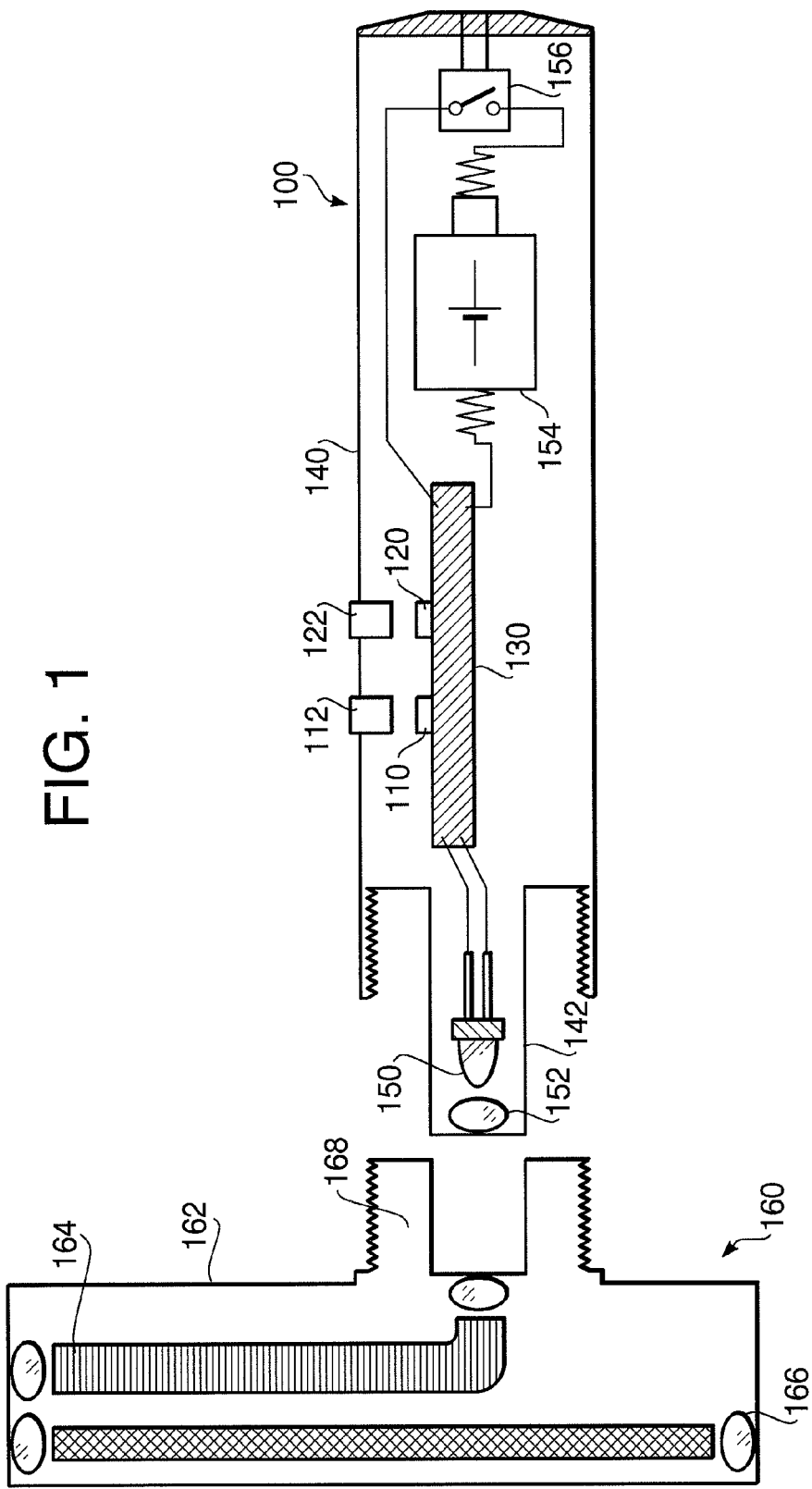

Embodiments according to aspects of the present invention will be described with reference to the accompanying drawings. FIG. 1 schematically shows a cross section of an endoscope using an operating state display system in a first embodiment according to aspects of the present invention. Explanations of elements that are not directly related to the present invention will be omitted.

An endoscope 160 includes an observation optical system 166 for observing a subject and an illumination optical system 164 for transmitting light for illuminating the observed subject. The illumination optical system 164 transmits light emitted by a light source apparatus 100 attached to a light source joint portion 168 and illuminates the observed subject. The observation optical system 166 causes light reflected by the observed subject to be transmitted therethrough, and an operator visually catches the reflected light, observing the observed subject.

The light source apparatus 100 has a lens 152 and an illumination LED 150 as an illuminating light source at a distal end portion 142. There is provided at the distal end portion 142 a detection switch (not shown) configured to detect whether the distal end portion 142 is attached to the light source joint portion 168. When a main switch 156 is set ON while the detection switch is detecting that the distal end portion 142 is attached to the light source joint portion 168, an electrical current is supplied to a control circuit (not shown) provided on a control circuit board 130 from a battery 154. Thereby, the electrical current is supplied to the illumination LED 150 so that the illumination LED 150 can light. Light emitted by the illumination LED 150 is converged by the lens 152 and directed to the illumination optical system 164.

There is provided on the control circuit board 130 the control circuit that causes the illumination LED 150 to emit light. The control circuit includes a booster circuit for boosting a voltage supplied by the battery 154 and an operating state display circuit for lighting first and second LEDs 110 and 120 depending on the voltage 154 supplied by the battery.

The booster circuit applies the boosted voltage to the illumination LED 150 to light the illumination LED 150. The operating state display circuit is provided with the first and second LEDs 110 and 120 attached to the control circuit board 130, a voltage detector (not shown), and a transistor (not shown). The voltage detector, connected with the battery 154, detects the voltage of the battery 154. A detection voltage of the voltage detector is 2.1 V. When the voltage supplied by the battery is more than the detection voltage, the voltage detector outputs a voltage. A plurality of transistors are operated by difference between the output voltage of the voltage detector and the output voltage of the battery 154, so that a voltage can be applied to the first LED 110 and/or the second LED 120. Thereby, when the output voltage of the battery 154 is over 2.2 V, the first LED 110 emits green light. Meanwhile, when the output voltage of the battery 154 is less than 2.2 V and more than 2.1 V, the second LED 120 emits yellow light.

The light emitted by the first and second LEDs 110 and 120 is introduced out of the light source apparatus 100 via first and second light guiders 112 and 122 that are attached to a housing 140 to be exposed out of an outer surface of the housing 140, respectively.

A configuration of the operating state display system will be explained with reference to FIGS. 2 and 3. In general, an LED has directional characteristics as shown in FIG. 3. In FIG. 3, an iso-intensity line 310 indicated by an oval represents positions with a light intensity of half as high as that in a luminous point of the LED. A leak light beam 240 shown in FIG. 3 corresponds to a leak light beam 240 shown in FIG. 2. Meanwhile, a light intensity area line 242 shown in FIG. 3 corresponds to a light intensity area line 242 shown in FIG. 2.

The first LED 110 is attached on the control circuit board 130 provided inside the housing 140. The first light guider 112 is provided to face the first LED 110.

The first light guider 112, shaped as a cylinder, is attached to the housing 140 so as to penetrate the housing 140 from an inside to an outside of the housing 140 along an axial direction of the first light guider 112 as a cylinder. The first light guider 112 has a circular first light emitting surface 214 on one end surface thereof and a circular first light receiving surface 216 on the other end surface thereof. The first light emitting surface 214 is exposed out of the housing 140. The first light receiving surface 216 faces the first LED 110.

The light emitted by the first LED 110 is incident onto the first light receiving surface 216 of the first light guider 112. The incident light is transmitted through the first light guider 112 and emitted from the first light emitting surface 214 out of the first light guider 112.

The second LED 120 is attached on the control circuit board 130 to be adjacent to the first LED 110. The second light guider 122 is formed in a cylindrical shape in the same manner as the first light guider 112. The second light guider 122 is attached to the housing so as to penetrate the housing 140 from the inside to the outside of the housing 140. The second light guider 122 has a circular second light emitting surface 224 on one end surface thereof and a circular second light receiving surface 226 on the other end surface thereof. The second light emitting surface 224 is exposed out of the housing 140. The second light receiving surface 226 faces the second LED 120.

The light emitted by the second LED 120 is incident onto the second light receiving surface 226 of the first light guider 112. The incident light is transmitted through the second light guider 122 and emitted from the second light emitting surface 224 out of the second light guider 122.

An electronic component 260, formed in a rectangular parallelepiped shape or a cylindrical shape, is attached between the first and second LEDs 110 and 120 on the control circuit board 130. For example, a chip condenser is employed as the electronic component 260. The electronic component 260 is configured to protrude from a surface of the control circuit board 130 by a predetermined length in the same direction as the first and second LEDs 110 and 120. The aforementioned predetermined length is longer than a distance between the first light receiving surface 216 and the control circuit board 130 and a distance between the second light receiving surface 226 and the control circuit board 130.

Figure 2:
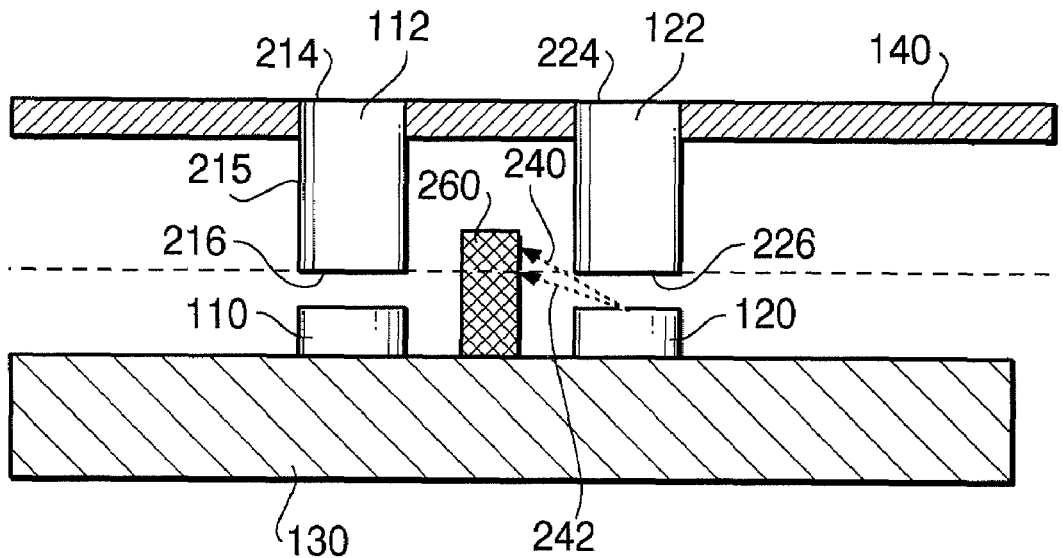
Figure 3:
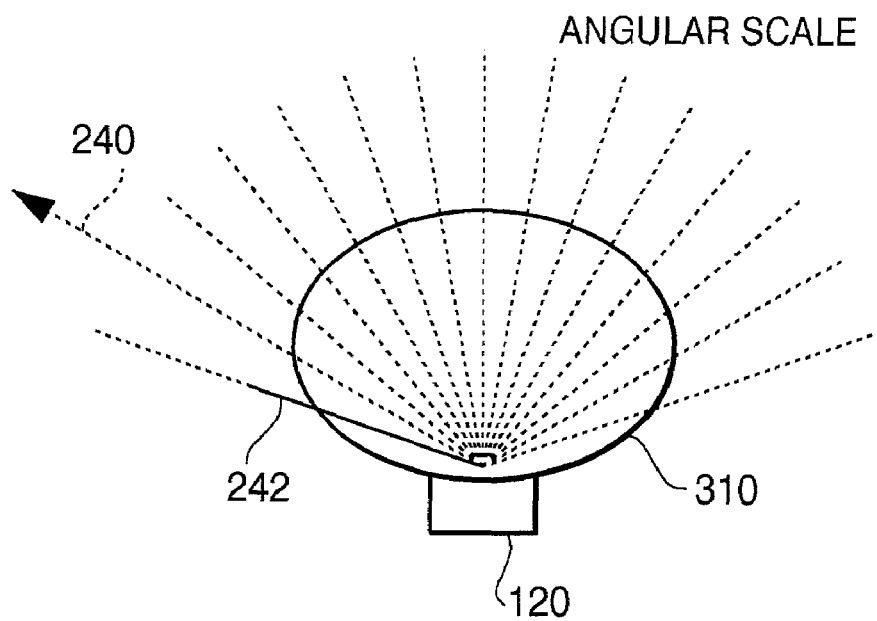

The electronic component 260 has a predetermined constant width in a direction (width direction) in which the first and second light guiders 112 and 122 are aligned, namely, a horizontal direction in FIG. 2. In addition, the electronic component 260 has a predetermined depth more than those of the first and second light guiders 112 and 122 in a direction (depth direction) perpendicular to both a longitudinal direction and horizontal direction in FIG. 2. Further, the electronic component 260 is located at a midpoint between the first and second light guiders 112 and 122 in the aforementioned width direction thereof, and arranged to cover over the first and second light guiders 112 and 122 in the aforementioned depth direction.

A portion of the light emitted by the second LED 120 that is directed to the first light guider 112 is blocked by the electronic component 260 so as not to reach the first light guider 112.

Further, a portion of the light emitted by the second LED 120 that is not blocked by the electronic component 260 may illuminate a first transmission surface 215. In this case, an illuminated area on the first transmission surface 215 is located out of a region surrounded by the iso-intensity line 310 for the second LED 120 as shown in FIG. 3. In other words, the first transmission surface 215 is not provided within a region where the light emitted by the second LED 120 has a light intensity higher than half of the light intensity in a luminous point of the second LED 120. Therefore, light with a light intensity higher than half of the light intensity in the luminous point of the second LED 120 cannot be incident onto the first transmission surface 215. When the first transmission surface 215 is arranged as above, a portion of the light emitted by the second LED 120 that is incident onto the first transmission surface 215 has a light intensity equal to or lower than half of the light intensity in the luminous point of the second LED 120. The light incident to the first transmission surface 215 is introduced to the first light emitting surface 214 by the first light guider 112 and emitted from the first light emitting surface 214 out of the first light guider 112.

The second light receiving surface 226 of the second light guider 122 is provided within the region surrounded by the iso-intensity line 310 for the second LED 120. That is, the second light receiving surface 226 is located in a position where the light emitted by the second LED 120 has a light intensity higher than half of the light intensity in the luminous point of the second LED 120. With the second light receiving surface 226 being arranged as above, light with a high light intensity is incident onto the second light receiving surface 226. Thereby, there is emitted from the second light emitting surface 224 light with such a high light intensity that the operator can visually recognize the light with ease.

Hence, the light emitted from the first light emitting surface 214 has a light intensity lower than that of the light emitted from the second light emitting surface 224. Accordingly, the operator can avoid making a wrong judgment that light is emitted from the first light emitting surface 214. Additionally, it is possible to prevent leak light from the first LED 110 or the second LED 120 without a light shielding plate separately provided, and thereby the operator can properly know the remaining battery level.

In the first embodiment, the electronic component 260 is located at the midpoint between the first and second light guiders 112 and 122 in the width direction thereof. However, the location of the electronic component 260 is not limited to the midpoint between the first and second light guiders 112 and 122. Namely, when the electronic component 260 is so high as to prevent leak light from one of the LEDs 110 and 120 from being incident to the light guider corresponding to the other LED, the electronic component 260 may be located closer to one of the first and second light guiders 112 and 122 than to the other. In this case, the same effects as the aforementioned first embodiment can be expected.

Figure 4:
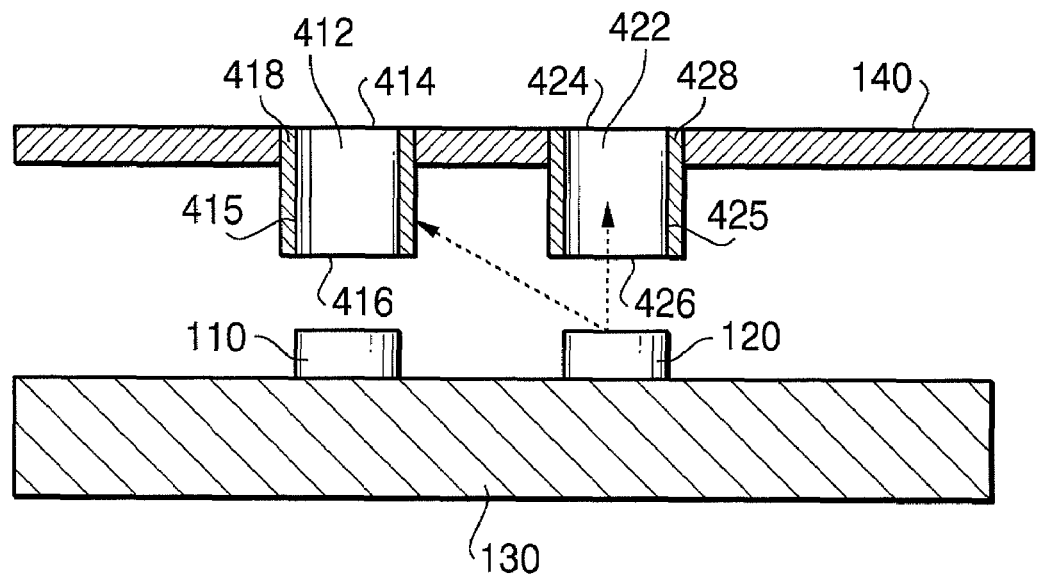
FIG. 4 is a cross-sectional side view of an operating state display system in a second embodiment according to one or more aspects of the present invention.
Figure 5:
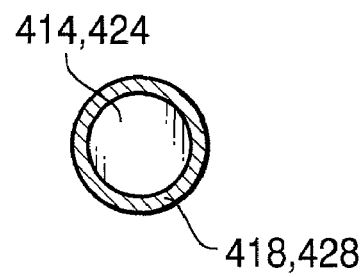
FIG. 5 is a cross-sectional view of a light guider employed in the operating state display system in the second embodiment according to one or more aspects of the present invention.

Subsequently, a second embodiment will be described with reference to FIGS. 4 and 5. Explanations on the same constitutions as the first embodiment will be omitted.

In the second embodiment, first and second light guiders 412 and 422 each of which is formed as a cylindrical shape have first and second transmission surfaces 415 and 425 as outer circumferential surfaces thereof, respectively. An optical treatment for preventing optical transmission is performed for each of the first and second transmission surfaces 415 and 425.

As the optical treatment for preventing optical transmission, an anti-transmission film is formed on each of the first and second transmission surfaces 415 and 425. For instance, coating films 418 and 428 are formed by applying black coating material on the first and second transmission surfaces 415 and 425, respectively. The coating film 418 absorbs or reflects light emitted to the first transmission surface 415 of the first light guider 412 by the second LED 120, so that a light intensity of light incident inside the first light guider 412 can drastically be reduced. Thereby, even though the light incident onto the first transmission surface 415 reaches a first light emitting surface 414 and is emitted from the first light emitting surface 414 out of the first light guider 412, the light intensity of the emitted light is very low. Accordingly, the operator can avoid making a wrong judgment that light is emitted from the first light emitting surface 414 of the first light guider 412.

According to the aforementioned embodiments, the operator can properly recognize which LED lights and know a proper remaining battery level.

In the second embodiment, the optical treatment may be performed by applying coating material on the first and second transmission surfaces 415 and 425 or by putting respective covers such as resin tubes and self-contractile tubes on the first and second transmission surfaces 415 and 425.

The present disclosure relates to the subject matter contained in Japanese Patent Application No. P2006-272376, filed on Oct. 4, 2006, which is expressly incorporated herein by reference in its entirety.

What is claimed is:

1. An operating state display system, comprising:
   a housing;
   a board provided inside the housing;
   a first light emitter attached on the board;
   a second light emitter arranged adjacent to the first light emitter on the board;
   a first light guider attached to the housing to face the first light emitter such that light emitted by the first light emitter is transmitted therethrough to be emitted out of the housing;
   a second light guider attached to the housing to face the second light emitter such that light emitted by the second light emitter is transmitted therethrough to be emitted out of the housing; and
   an electronic component attached between the first and second light emitters on the board, the electronic component being configured to protrude from a surface of the board by a predetermined length in the same direction as the first and second light emitters, the predetermined length being longer than a distance between the first light emitter and the board and a distance between the second light emitter and the board.

2. The operating state display system according to claim 1, wherein the first light guider is arranged such that a portion thereof illuminated by the light emitted by the second light emitter is located out of a region where the light emitted by the second light emitter has a light intensity higher than half of a light intensity in a luminous point of the second light emitter.

3. The operating state display system according to claim 2, wherein the second light guider is arranged such that a portion thereof illuminated by the light emitted by the first light emitter is located out of a region where the light emitted by the first light emitter has a light intensity higher than half of a light intensity in a luminous point of the first light emitter.

4. The operating state display system according to claim 1, wherein the first light guider includes a first light receiving surface that faces the first light emitter to receive the light emitted by the first light emitter and a first light emitting surface exposed out of the housing to emit the light received by the first light receiving surface out of the housing; and
   wherein the second light guider includes a second light receiving surface that faces the second light emitter to receive the light emitted by the second light emitter and a second light emitting surface exposed out of the housing to emit the light received by the second light receiving surface out of the housing.

5. The operating state display system according to claim 1, wherein each of the first and second light guiders is formed in a cylinder shape,
   wherein the first light guider includes a first transmission surface as a side surface of the cylinder, and
   wherein the second light guider includes a second transmission surface as a side surface of the cylinder.

6. The operating state display system according to claim 1, wherein the electronic component is configured to cover over the first and second light emitters in a direction that is perpendicular to an arranging direction of the first and second light guiders and parallel to the surface of the board.

7. The operating state display system according to claim 1, wherein the electronic component is formed in one of a rectangular parallelepiped shape and a cylinder shape.

8. The operating state display system according to claim 1, wherein the electronic component includes a chip condenser.

9. An operating state display system, comprising:
   a housing;
   a board provided inside the housing;
   a first light emitter attached on the board;
   a second light emitter arranged adjacent to the first light emitter on the board;
   a first light guider attached to the housing, the first light guider including:
      a first light receiving surface that faces the first light emitter to receive light emitted by the first light emitter;
      a first light emitting surface exposed out of the housing to emit the light received by the first light receiving surface out of the housing; and
      a first transmission surface; and
   a second light guider attached to the housing, the second light guider including:
      a second light receiving surface that faces the second light emitter to receive light emitted by the second light emitter;
      a second light emitting surface exposed out of the housing to emit the light received by the second light receiving surface out of the housing; and
      a second transmission surface, and
   wherein the first and second transmission surfaces are configured to block externally incident light.

10. The operating state display system according to claim 9, wherein each of the first and second transmission surfaces is configured with coating material being applied thereon to block the externally incident light.

11. The operating state display system according to claim 9, wherein each of the first and second transmission surfaces is configured with a cover being put thereon to block the externally incident light.

* * * * *

UNITED STATES PATENT AND TRADEMARK OFFICE
CERTIFICATE OF CORRECTION

PATENT NO.         : 7,490,968 B2                                      Page 1 of 1
APPLICATION NO.    : 11/865870
DATED              : October 2, 2007
INVENTOR(S)        : Satoshi Takami et al.

It is certified that error appears in the above-identified patent and that said Letters Patent is hereby corrected as shown below:

On the cover sheet of the printed patent, the heading --Foreign Application Priority Data--, should be included, and --JP 2006-272376  October 4, 2006-- should be listed thereunder.

Signed and Sealed this

Second Day of June, 2009

JOHN DOLL
*Acting Director of the United States Patent and Trademark Office*

UNITED STATES PATENT AND TRADEMARK OFFICE
CERTIFICATE OF CORRECTION

PATENT NO.        : 7,490,968 B2                                      Page 1 of 1
APPLICATION NO.   : 11/865870
DATED             : February 17, 2009
INVENTOR(S)       : Satoshi Takami et al.

It is certified that error appears in the above-identified patent and that said Letters Patent is hereby corrected as shown below:

On the cover sheet of the printed patent, the heading --Foreign Application Priority Data--, should be included, and --JP 2006-272376  October 4, 2006-- should be listed thereunder.

This certificate supersedes the Certificate of Correction issued June 2, 2009.

Signed and Sealed this

Twenty-third Day of June, 2009

JOHN DOLL
*Acting Director of the United States Patent and Trademark Office*